United States Patent
Moody

(10) Patent No.: US 8,039,662 B2
(45) Date of Patent: Oct. 18, 2011

(54) PROCESS FOR THE PREPARATION OF AMINO ACID METHYL ESTERS

(75) Inventor: Harold Monro Moody, Gulpen (NL)

(73) Assignee: DSM IP Assets B.V., Heerlen (NL)

( * ) Notice: Subject to any disclaimer, the term of this patent is extended or adjusted under 35 U.S.C. 154(b) by 27 days.

(21) Appl. No.: 12/528,691

(22) PCT Filed: Mar. 10, 2008

(86) PCT No.: PCT/EP2008/052814
§ 371 (c)(1),
(2), (4) Date: Aug. 26, 2009

(87) PCT Pub. No.: WO2008/110529
PCT Pub. Date: Sep. 18, 2008

(65) Prior Publication Data
US 2010/0063312 A1   Mar. 11, 2010

(30) Foreign Application Priority Data
Mar. 9, 2007   (EP) .................................... 07103851

(51) Int. Cl.
*C07C 229/00*   (2006.01)

(52) U.S. Cl. ...................................................... 560/155
(58) Field of Classification Search ................. None
See application file for complete search history.

(56) References Cited

U.S. PATENT DOCUMENTS 3,978,034 A * 8/1976 Sheehan et al. ............... 560/125
4,680,403 A   7/1987 Hisamitsu et al.
5,113,009 A * 5/1992 Ajioka et al. ................... 560/40

FOREIGN PATENT DOCUMENTS
EP   0 544 205   6/1993

OTHER PUBLICATIONS
International Search Report for PCT/EP2008/052814, mailed Jun. 11, 2008.

* cited by examiner

*Primary Examiner* — Paul A Zucker
(74) *Attorney, Agent, or Firm* — Nixon & Vanderhye P.C.

(57) ABSTRACT

The present invention describes a process for the synthesis of an amino acid methyl ester comprising the following steps: (a) refluxing a reaction mixture comprising a free amino acid, methanol and a strong acid; (b) concentrating the mixture; (c) adding methanol; (d) repeating steps a-c one or more times.

4 Claims, No Drawings

PROCESS FOR THE PREPARATION OF AMINO ACID METHYL ESTERS

This application is the U.S. national phase of international Application No. PCT/EP2008/052814, filed 10 Mar. 2008, which designated the U.S. and claims priority to Europe Application No. 07103851.7, filed 9 Mar. 2007, the entire contents of each of which are hereby incorporated by reference.

The present invention relates to a process for the preparation of amino acid methyl esters.

A method of esterifying amino acids with sulfuric acid as the catalyst is known from U.S. Pat. No. 4,680,403. The process involves heating an amino acid in an alcohol in the presence of sulfuric acid. A serious drawback of this process is that the yields are rather low. In EP-A-0544205, the process has been modified in order to obtain higher yields. In this modified process, the major part of the alcohol is added as a liquid or a gas to the reaction mixture composed of the amino acid, a minor part of the alcohol and sulfuric acid, while at the same time, the same amount of alcohol is distilled off from the reaction mixture. The inventors report high yields compared to the process according to U.S. Pat. No. 4,680,403. A major drawback of the process disclosed in EP-A-0544205 is the high consumption of alcohol (up to 8-fold) compared to the U.S. Pat. No. 4,680,403 process. This high consumption of alcohol makes the process economically very unattractive.

It is an object of the present invention to provide a cost effective process for the synthesis of methyl esters of amino acids wherein the synthesis has a high yield as well as a low consumption of alcohol.

"Amino acid" is defined herein as an organic molecule having at least one carboxylic acid group COOH and one amino group ($NH_2$). These groups may be attached to the same carbon atom of the organic molecule as in alpha amino acids, or to different carbon atoms such as in beta amino acids, gamma-amino acids etceteras. The amino acid may be any optical isomer, i.e. the dextorotary (D), levorotary (L) or racemic (D,L) form. Alpha-amino acids have a central carbon atom with the following constituents attached to it: a carboxylic acid group COOH, an amino group ($NH_2$), hydrogen (H) and a group R according to the following formulae:

R—HC($NH_2$)—COOH

Examples of such alpha-amino acids are the twenty L-alpha amino acids which are found in Nature and which make up proteins: glycine, alanine, valine, leucine, isoleucine, threonine, proline, histidine, serine, cystein, methionine, phenylalanine, tyrosine, tryptophane, arginine, lysine, glutamine, glutamic acid, asparagine, aspartic acid. Other examples are amino acid used for the synthesis of semi-synthetic beta-lactam antibiotics such as D-phenylglycine, D-dihydro-phenylglycine, D-4-hydroxyphenylglycine and others.

"Free amino acid" is defined herein as the unesterified form of the amino acid, i.e. with a free carboxyl group.

"Amino acid methyl ester" is defined herein as the methyl ester form of the amino acid whereby the carboxyl group of the amino acid is esterified to an alcohol, for instance D-phenylglycine methyl ester, D-dihydro-phenylglycine methyl ester or D-4-hydroxy-phenylglycine methyl ester.

"Ratio" is defined herein as:

$$\frac{[\text{Amount of amino acid methyl ester}]}{[\text{Amount of amino acid }methylester] + [\text{Amount of free amino acid}]}$$

whereby the amounts are expressed in moles

In one aspect, the invention provides a process for the synthesis of an amino acid methyl ester comprising the following steps:
a. refluxing a reaction mixture comprising a free amino acid, methanol and a strong acid;
b. concentrating the mixture obtained in step (a);
c. adding methanol;
d. repeating steps (a)-(c) one or more times.

An initial reaction mixture is made by mixing suitable amounts of free amino acid, methanol and a strong acid. The volume of this initial mixture is referred to herein as the initial reaction volume.

The amino acid in the process of the invention may be any amino acid as defined herein. Preferred are the alpha-amino acids, in particular those alpha amino acids of which the methyl esters may be used for the synthesis of semi-synthetic beta-lactam antibiotics such as D-phenylglycine, D-dihydro-phenylglycine, D-4-hydroxy-phenylglycine and others.

Preferably the following molar ratio of methanol relative to free amino acid is used in the initial reaction mixture: between 3 and 25, more preferably between 5 and 25 and most preferably between 6 and 10. The strong acid may be any strong acid such as hydrochloric acid, sulphuric acid, alkyl- or arylsulfonic acid; preferred are sulphuric acid, methanesulfonic acid and para-toluenesulfonic acid, most preferred is sulphuric acid. Preferably the following molar ratio of strong acid (in equivalents, e.g. one mole of hydrochloric acid is one equivalent and one mole of sulfuric acid is two equivalents) relative to free amino acid chain is used: between 0.9 and 10, more preferably between 1 and 5 and most preferably between 2 and 3. The skilled person will be able to optimize the reaction conditions depending on the amino acid selected without undue experimentation.

The refluxing step may be carried out for a certain time, for example between between 0.5 and 5 hours, preferably between 1 hour and 3 hours, more preferably between the 1.5 and 2.5 hours at a temperature between 20 and 100° C., more preferably between 40 and 100° C., more preferably between 60 and 100° C., most preferably between 60 and 80° C.

During the concentrating step (b), methanol and water are removed by evaporation. The pressure during this step may initially be atmospheric and may during the concentrating step be reduced, for instance by a vacuum pump, to preferably 50 mbar or less, more preferably to 40 mbar or less, more preferably to 30 mbar or less and most preferably to 20 mbar or less. As a result of the evaporation of methanol and water, the temperature may initially drop, for instance to 40° C. and rise again during the concentrating step (b). In general, the concentrating step (b) may be carried out at a temperature between 40 and 100° C., preferably between 60 and 90° C., more preferably between 70 and 80° C. The concentrating step is continued until more than 30% of the water present before the concentrating step is removed, preferably more than 40% of the water is removed, preferably more than 50% of the water is removed, preferably more than 70% of the water is removed, preferably more than 80% of the water is removed and most preferably more than 90% of the water is removed.

After the concentrating step, a suitable amount of methanol is added (step (c)), preferably an amount so as to obtain the initial volume of the reaction mixture or an amount which is less than the initial volume of the reaction mixture, e.g. ≦90% or ≦80% or ≦70% or ≦60% or ≦50% or ≦40% or ≦30% or ≦20% of the initial volume of the reaction mixture. The amount of methanol added may also be more than the initial volume of the reaction mixture. Step (a), (b) and (c) are repeated one or more times, at least once, preferably 2 times, more preferably 3 times, more preferably 4 times, more preferably 5 times, more preferably 6 times, more preferably 7 times, more preferably 8 times, more preferably 9 times, more preferably 10 times. It was found that by repeating these steps the 'ratio" as defined hereinbefore of the formation of amino acid methyl ester increased significantly. For instance, after carrying out steps (a)-(c) only once, a "ratio" between 75-85% may be obtained, after repeating steps (a)-(c) once, a "ratio" between 85-95% may be obtained, and after repeating steps (a)-(c) 2 times, a "ratio" between 95-97% may be obtained, and after repeating steps (a)-(c) 3 times, a "ratio" between 97-98% may be obtained and after repeating steps (a)-(c) 4 times, a "ratio" between 98-99% may be obtained and after repeating steps (a)-(c) 5 times, a "ratio" between 99-99.5% may be obtained and after repeating steps (a)-(c) more than 5 times a "ratio of more than 99.5% may be obtained.

Optionally, the mixture obtained after step (b) or step (c) may be further purified so as to obtain a mixture with a high "ratio" as defined hereinbefore. The ratio of the mixture is preferably ≧85%, more preferably ≧90%, more preferably ≧95%, more preferably ≧96%, more preferably ≧97%, more preferably ≧98%, more preferably ≧99% more preferably ≧99.5%, most preferably ≧99.8%.

One embodiment of the purification step involves the precipitation and removal of the free amino acid from the amino acid ester. This may be achieved by adjusting the pH of the mixture obtained in step (a) to a value between 2 and 6.5, preferably between 2.5 and 5, most preferred between 3 and 4 by adding a suitable base, such as NaOH, ammonia, KOH. In another embodiment, the reaction mixture obtained in step (a) may be added to a suitable amount of water or to an alcohol or to a mixture of water and alcohol, followed by adjusting the pH to a value between 2 and 6.5, preferably between 2.5 and 5, most preferred between 3 and 4 by adding a suitable base, such as NaOH, ammonia, KOH. After adjusting the pH to the desired value, the pH may be maintained at the desired value by adding the suitable base. Under these conditions, a precipitate comprising the free amino acid may be formed. After a suitable time, the precipitate may be filtered off using known techniques. The filtrate comprises the amino acid methyl ester. The pH of the filtrate may be brought to a pH between 1 and 6, preferably between 1 and 4, most preferably between 1.5 and 3, after which the alcohol may be removed by evaporation using known techniques.

Another embodiment of purification step involves the formation of a two or multi-phase system comprising an organic phase containing the amino acid methyl ester derivative and a minor amount of free amino acid and an aqueous phase containing the free amino acid and, optionally, salt. This may be achieved by adjusting the pH of the mixture obtained in step (a) at a value between 7.5 and 10, preferably between 8.5 and 9.5, most preferred between 8.8 and 9.2 by adding a suitable base, such as NaOH, ammonia, KOH. In another embodiment, the reaction mixture obtained in step (a) may be added to a suitable amount of water, an alcohol or to a mixture of water and alcohol, followed by adjusting the pH at a value between 7.5 and 10, preferably between 8.5 and 9.5, most preferred between 8.8 and 9.2 by adding a suitable base, such as NaOH, ammonia, KOH. After adjusting the pH to the desired value, the pH may be maintained at the desired value by adding the suitable base. Optionally, the water may be in the form of an aqueous salt (e.g. NaCl) solution. The free amino acid may also form a precipitate. The various phases in the multi-phase system may be separated using known techniques. Optionally the organic phase may be washed with water or an aqueous salt solution. The water phase of the wash may be recycled to a suitable process stream in order to avoid loss of yield. This process stream may be the reaction mixture as obtained after step (a) or the after the pH adjustment as described.

A highly preferred embodiment of purification step combines the 2 previous embodiments, i.e. first adjusting the pH of the mixture obtained in step (a) between 2 and 6.5, preferably between 2.5 and 5, most preferred between 3 and 4 and filtering off the precipitate formed and subsequently adjusting the pH of the filtrate obtained at a pH between 7.5 and 10, preferably between 8.5 and 9.5, most preferred between 8.8 and 9.2 and separating the various phases in the multi-phase system obtained using known techniques.

EXAMPLES

Comparative Example

Synthesis of a D-phenylglycine-methylester (PGM) Solution with Continuous Addition and Distillation of Methanol This experiment was carried out essentially as described in EP-A-0544205 with the following modifications: D-phenylglycine was used instead of L-phenylalanine or L-aspartic acid or L-valine as in EP-A-0544205 and the temperature was lower (73° C. instead of 85-90° C. in EP-A-0544205).

135 g D-phenylglycine was suspended in 252 ml (200 g) methanol and 107 g concentrated sulphuric acid was added. The mixture was kept at reflux for 2 hours at approximately 73° C. The reactor was equipped with a tapped reflux/distillation unit. Under conditions of reflux the tap is closed while during distillation the tap is open. Dry methanol was dosed into the reactor at a dosage speed of 110 g/h. The level inside the reactor was kept constant by distilling off at the same rate (tap open). The results are shown in Table 1. After addition of 708 g methanol, the ratio (as defined hereinbefore) was 91.0%. Even after adding 2400 g methanol, the ratio increased to only 94.7%.

TABLE 1

| Comparative example | | Example 1 | |
|---|---|---|---|
| Total amount of methanol added (g) | Ratio (%) | Total amount of methanol added (g) | Ratio (%) |
| 200 | 79.7 | 200 | 82.2 |
| 236 | 80.6 | | |
| 292 | 82.6 | 300 | 93.3 |
| 358 | 85.3 | | |
| 421 | 87.3 | 400 | 96.4 |
| 529 | 89.3 | 500 | 97.7 |
| 544 | 90.2 | | |
| 596 | 91.0 | 600 | 98.7 |
| 650 | 91.3 | | |
| 708 | 91.0 | 700 | 99.2 |
| 901 | 92.2 | | |
| 1398 | 93.5 | | |
| 1908 | 94.3 | | |
| 2400 | 94.7 | | |

Example 1

Synthesis of a D-phenylglycine-methylester (PGM) Solution 135 g D-phenylglycine was suspended in 252 ml (200 g) methanol and 107 g concentrated sulphuric acid was added. The mixture was kept at reflux for 2 hours at approximately 73° C. and concentrated at a reduced pressure using a vacuum pump. The pressure dropped from atmospheric to 20 mBar while at the same time the temperature of the reaction mixture increased from 40 to 80° C.

A second portion of 126 ml (100 g) methanol was added; the mixture was kept at reflux for 1 hour at approximately 81° C. and again concentrated at a reduced pressure as described above. The procedure was repeated for another three times (adding methanol, refluxing and concentrating). Finally, 126 ml (100 g) methanol was added and the solution was refluxed for another hour and cooled to ambient temperature. The results are shown in Table 1. The final ratio was 99.2% and 700 g methanol had been consumed.

Subsequently, 15 ml ammonia was added at a constant rate in 35 min until the pH was 2.3-2.4. Then, 75 ml water was added and the methanol was distilled off at a reduced pressure and while keeping the temperature below 50° C. The pH of the final PGM solution was 2.0.

When comparing the results of Example 1 with the Comparative Example, it can be concluded that the prior art method of the Comparative Example (continuous addition and distilling of methanol) gives a much lower "ratio" (94.7%) compared to the method used in Example 1 (99.2%). Furthermore, the prior art method consumes much more methanol for the same "ratio". For instance, to obtain a (low) "ratio" of 93%, in the Comparative Example approximately 1400 g of methanol is used, while in Example 1 only 300 g is used which is only 21%.

Example 2

Synthesis of a D-phenylglycine-methylester (PGM) Solution 90 g D-phenylglycine was suspended in 170 ml methanol and 73.2 g concentrated sulphuric acid was added. The mixture was kept at reflux for 2 hours at approximately 73° C. and concentrated at a reduced pressure using a vacuum pump. The pressure dropped from atmospheric to 20 mBar while at the same time the temperature of the reaction mixture increased from 40 to 80° C.

170 ml methanol was added and the mixture was kept again at reflux for 2 hours and concentrated at reduced pressure. Again, 170 ml methanol was added and the mixture was kept at reflux for 2 hours and concentrated at reduced pressure. Finally, 125 ml methanol was added. At this stage, the "ratio" as defined hereinbefore was 95%.

The solution was dosed into a second reactor, which had been pre-charged with 20 ml methanol, in 1 hour at 20° C. The pH was kept at 3.5 with ammonia. A solid was formed, which was removed by filtration. The resulting mother liquor was diluted with 25 ml water and concentrated at reduced pressure (p=20 mm Hg, T=40-45° C.). Finally 207.5 g phenylglycine-methylester (PGM) solution was obtained. The "ratio" of the resulting solution was 99%.

Example 3

Synthesis of D-dihydrophenylglycine-methylester (DHPGM) Solution 90 g D-dihydrophenylglycine (DHPG) was suspended in 200 ml methanol and 73.2 g concentrated sulphuric acid was added. The mixture was kept at reflux for 2 hours at 73° C. and concentrated at a reduced pressure using a vacuum pump. The pressure dropped from atmospheric to 20 mBar while at the same time the temperature of the reaction mixture increased from 40 to 80° C.

170 ml methanol was added and the mixture was kept again at reflux for 2 hours and concentrated at reduced pressure. Again, 170 ml methanol was added and the mixture was kept at reflux for 2 hours and concentrated at reduced pressure. Finally, 125 ml methanol was added. At this stage, the "ratio" as defined herein before was 94.8%.

The solution was dosed into a second reactor, which had been pre-charged with 20 ml methanol, in 1 hour at 20° C. The pH was kept at 3.5 with ammonia. A solid was formed, which was removed by filtration. The resulting mother liquor was diluted with 25 ml water, decolorized with 3 g charcoal (activated carbon) and concentrated at reduced pressure (p=20 mm Hg, T=40-45° C.). Finally 217.6 g DHPGM solution was obtained. The "ratio" of the resulting solution was 99.2%.

The invention claimed is:

1. Process for the synthesis of an amino acid methyl ester comprising the following steps:
   (a) refluxing a reaction mixture comprising a free amino acid, methanol and a strong acid at a temperature between 40 and 100° C.;
   (b) while maintaining the temperature of the mixture of step (a) of between 40 and 100° C. concentrating the mixture obtained in step (a) to obtain a concentrated mixture thereof;
   (c) adding methanol to the concentrated mixture obtained in step (b); and
   (d) repeating steps (a)-(c) one or more times.

2. Process according to claim 1 wherein steps (a)-(c) are repeated at least 2 times.

3. Process according to claim 1 wherein the amino acid is an alpha-amino acid which is selected from the group consisting of D-phenylglycine, D-dihydro-phenylglycine and D-4-hydroxy-phenylglycine.

4. Process according to claim 1 wherein the strong acid is sulphuric acid.

* * * * *